(12) United States Patent
Crawford et al.

(10) Patent No.: US 10,982,337 B2
(45) Date of Patent: Apr. 20, 2021

(54) CORROSION INHIBITION

(71) Applicant: SCHLUMBERGER TECHNOLOGY CORPORATION, Sugar Land, TX (US)

(72) Inventors: Lynne Patricia Crawford, Cambridge (GB); Evgeny Borisovich Barmatov, Cambridge (GB); Trevor Lloyd Hughes, Cambridge (GB); Man Yi Ho, Cambridge (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 0 days.

(21) Appl. No.: 15/769,460

(22) PCT Filed: Oct. 17, 2016

(86) PCT No.: PCT/US2016/057259
§ 371 (c)(1),
(2) Date: Apr. 19, 2018

(87) PCT Pub. No.: WO2017/070026
PCT Pub. Date: Apr. 27, 2017

(65) Prior Publication Data
US 2018/0312980 A1 Nov. 1, 2018

(30) Foreign Application Priority Data
Oct. 19, 2015 (GB) ...................................... 1518417

(51) Int. Cl.
C23F 11/04 (2006.01)
C09K 8/54 (2006.01)
(Continued)

(52) U.S. Cl.
CPC ............ C23F 11/04 (2013.01); *C07D 209/08* (2013.01); *C07D 209/14* (2013.01);
(Continued)

(58) Field of Classification Search
None
See application file for complete search history.

(56) References Cited

U.S. PATENT DOCUMENTS 2,935,474 A 5/1960 Kirkpatrick et al.
3,081,304 A 3/1963 Rogier
(Continued)

FOREIGN PATENT DOCUMENTS

CN 101892042 A 11/2010
CN 102049213 A 5/2011
(Continued)

OTHER PUBLICATIONS

Chiang, L.Y. et al., "Chemistry of Catalytic Dehydrogenative Oligomerization of Tetrahydroquinoline and Structural Characterization of Nonsubstituted Quinolone Oligomers", Journal of the American Chemical Society, 1991, 113(17), pp. 6574-6584.
(Continued)

*Primary Examiner* — John J Figueroa

(57) ABSTRACT

A corrosion inhibiting compound with a general structure A-B or A-X-B for inhibition of corrosion of steel in acidic solution. A comprises a heterocyclic ring system having a plurality of cyclic Carbon atoms and at least one cyclic Nitrogen atom, wherein the at least one cyclic Nitrogen atom is neutral under neutral conditions and protonatable under acidic conditions. B comprises at least two unsaturated Carbon atoms. B may comprise a ring system or a polymerisable group.

15 Claims, 4 Drawing Sheets

(51) Int. Cl.
  *C07D 209/08* (2006.01)
  *C07D 209/14* (2006.01)
  *C07D 215/06* (2006.01)
  *C07D 215/08* (2006.01)
  *C07D 295/03* (2006.01)

(52) U.S. Cl.
  CPC ......... *C07D 215/06* (2013.01); *C07D 215/08* (2013.01); *C07D 295/03* (2013.01); *C09K 8/54* (2013.01)

(56) References Cited

U.S. PATENT DOCUMENTS

| | | | |
|---|---|---|---|
| 3,335,090 | A | 8/1967 | Davidowich et al. |
| 3,337,470 | A | 8/1967 | Davidowich et al. |
| 3,816,322 | A | 6/1974 | Griffin et al. |
| 3,854,959 | A | 12/1974 | Costain et al. |
| 3,876,371 | A | 4/1975 | Costain et al. |
| 4,028,268 | A | 6/1977 | Sullivan, 3rd et al. |
| 4,120,654 | A | 10/1978 | Quinlan et al. |
| 4,387,041 | A | 6/1983 | Hort et al. |
| 4,698,168 | A | 10/1987 | Briggs |
| 4,734,259 | A | 3/1988 | Frenier et al. |
| 4,880,907 | A | 11/1989 | Chiang |
| 4,946,849 | A | 8/1990 | Makler |
| 5,096,618 | A | 3/1992 | Frenier |
| 5,120,471 | A * | 6/1992 | Jasinski ............... C23F 11/04 252/389.54 |
| 5,158,693 | A | 10/1992 | Ramanarayanan et al. |
| 5,591,381 | A | 1/1997 | Walker |
| 5,697,443 | A | 12/1997 | Brezinski et al. |
| 5,756,004 | A | 5/1998 | Brezinski |
| 5,763,368 | A | 6/1998 | Brezinski |
| 5,976,416 | A | 11/1999 | Brezinski |
| 6,281,172 | B1 | 8/2001 | Warren et al. |
| 7,216,710 | B2 | 5/2007 | Welton et al. |
| 7,906,544 | B2 | 3/2011 | Melander et al. |
| 3,288,410 | A1 | 10/2012 | Ablordeppey |
| 3,318,085 | A1 | 11/2012 | Cassidy et al. |
| 10,087,530 | B2 | 10/2018 | Hughes et al. |
| 2004/0235674 | A1 | 11/2004 | Youngson et al. |
| 2010/0261623 | A1 | 10/2010 | Cassidy et al. |
| 2013/0112106 | A1 | 5/2013 | Malwitz et al. |
| 2013/0310282 | A1 | 11/2013 | Kulkarni et al. |
| 2014/0027675 | A1 | 1/2014 | Matulewicz et al. |
| 2015/0152329 | A1 | 6/2015 | Seetheraman et al. |
| 2017/0335467 | A1 | 11/2017 | Barmatov et al. |
| 2018/0135187 | A1 * | 5/2018 | Crawford ............... C23F 11/04 |

FOREIGN PATENT DOCUMENTS

| | | | |
|---|---|---|---|
| CN | 103014715 | A | 4/2013 |
| CN | 103865506 | A | 6/2014 |
| EP | 0080794 | A1 | 6/1983 |
| EP | 0187322 | A1 | 7/1986 |
| EP | 0212752 | A1 | 3/1987 |
| EP | 0243982 | A1 | 11/1987 |
| EP | 0328319 | A1 | 8/1989 |
| EP | 0623598 | A1 | 11/1994 |
| EP | 0869258 | A1 | 10/1998 |
| GB | 1434354 | A | 5/1976 |
| GB | 2529723 | A | 3/2016 |
| JP | 2000038689 | A | 2/2000 |
| JP | 2007291079 | A | 11/2007 |
| WO | 9602508 | A1 | 2/1996 |
| WO | 0123374 | A1 | 4/2001 |
| WO | 0242248 | A2 | 5/2002 |
| WO | 03105849 | A1 | 12/2003 |
| WO | 2004065351 | A1 | 8/2004 |
| WO | 2006035954 | A1 | 4/2006 |
| WO | 2006136262 | A1 | 12/2006 |
| WO | 2008157234 | A2 | 12/2008 |
| WO | 2010023638 | A1 | 3/2010 |

OTHER PUBLICATIONS

Chiang, L.Y. et al., "Novel Quaternary Salts of Quinolone Oligomer as Metal Surface Protective Materials against Acid Corrosion", Chemistry of Materials, 1992, 4(2), pp. 245-247.

Finsgar, M. et al., "Application of Corrosion Inhibitors for Steels in Acidic Media for the Oil and Gas Industry: A Review", Corrosion Science, vol. 86, May 9, 2014, pp. 17-41.

Foster, G. L. et al., "Acetylenic Corrosion Inhibitors", Industrial and Engineering Chemistry, vol. 51, Jul. 1, 1959, pp. 825-828.

Frenier, W. W. et al., "A-Alkenylphenones—A New Class of Acid Corrosion Inhibitors", Corrosion Science, National Associate of Corrosion Engineers, 1988, 44(9), pp. 590-598.

Frenier, W.W. et al., "Mechanism of Iron Oxide Dissolution—A Review of Recent Literature", paper 121, presented at the 39th Corrosion Forum, NACE International, Houston, Texas, U.S.A., 1984, pp. 663-668.

Frenier, W.W., "Acidizing Fluids Used to Stimulate High Temperature Wells Can be Inhibited Using Organic Chemicals", Society of Petroleum Engineers (SPE) paper 18468, presented at the SPE International Symposium on Oilfield Chemistry, Houston, Texas, USA., 1989, pp. 111-123.

Gamboa-Vujicic, G. et al., "Toxicity of the mitochondrial poison dequalinium chloride in a murine model system", Journal of Pharmaceutical Sciences, 1993, 82(3), pp. 231-235.

Hartwell, J. et al., "Some Quaternary Ammonium Salts of Heterocyclic Bases. III. Bis-Quaternary Ammonium Salts", Journal of the American Chemical Society, 1950, 72(5), pp. 2040-2044.

Hegazy, M.A., "A novel Schiff base-based cationic Gemini surfactant: Synthesis and effect on corrosion inhibition of carbon steel in hydrochloric acid solution", Corrosion Science, 2009, 51, pp. 2610-2618.

Kanbara, T. et al., "Preparation of New Redox-Active Quaternized Poly(quinolinium) and Poly(isoquinolinium) Salts Showing Viologen-like Redox Behaviour", Macromolecules, 1993, 26, pp. 1975-1979.

Komloova, M. et al., "Preparation, in vitro screening and molecular modelling of symmetrical bis-quinolinium cholinesterase inhibitors-implications for early Myasthenia gravis treatment", Bioorganic and Medicinal Chemistry Letters, 2011, 21, pp. 2505-2509.

Lowmunkhong, et al., "Tryptamine as a Corrosion Inhibitor of Mild Steel in Hydrochloric Acid Solution", Corrosion Science, 2010, vol. 52, pp. 30-36.

Meakins, R.J., "Inhibition of the Corrosion of Steel by Long-Chain n-Alkylisoquinolinium Compounds", British Corrosion Journal, 1973, 8, pp. 230-234.

Mishra, A. et al., "New push-pull type dendritic stilbazolium dyes: synthesis, photophysical and electrochemical investigation", Dyes and Pigments, 2004, 63(2), pp. 191-202.

Oguzie, E. et al., "Inhibitive effect of methyl green dye on the corrosion of low carbon steel in acidic media", Pigment & Resin Technology, 2009, 38(6), pp. 359-365.

Podobaev, N. I. et al., "A review of Acetylene Compounds and Inhibitors of Acid Corrosion of Iron", Protection of Metals, vol. 40, Jan. 1, 2004, pp. 7-13.

Rehim et al., "On the Corrosion Inhibition of Low Carbon Steel in Concentrated Sulphuric Acid Solutions. Part 1: Chemical and Electrochemical (AC and DC) Studies", Corrosion Science, 2008, vol. 50, pp. 2258-2271.

Schmitt, G. et al., "Effect of Corrosion Inhibitors on the Hydrogen Uptake of Steel in Hydrochloric Acid", Proceedings of the 5th European Symposium Corrosion Inhibitors, Ferrara, Italy, 1980, pp. 337-353.

Schmitt, G. et al., "Investigations on structural and electronic effects in acid inhibitors by AC impedance", Materials and Corrosion, 1985, 36(6), pp. 273-278.

Stern, M. "A Method for Determining Corrosion Rates from Linear Polarization Data", Corrosion, 1958, 14(9), pp. 440-444.

Stern, M. et al., "Electrochemical Polarization: I. Theoretical Analysis of the Shape of Polarization Curves", Journal of the Electrochemical Society 1957, 104, pp. 56-63.

(56) References Cited

OTHER PUBLICATIONS

Tu et al., "Synthesis of N-Alkyl-4-(Hydroxybut-2-YNYL) Pyridinium Bromides and Their Corrosion Inhibition Activities on X70 Steel in 5 M HCI", Corrosion Science, 2012, vol. 65, pp. 13-25.
Vasilevsky et al., "Synthesis and Properties of Acetylenic Derivatives of Pyrazoles", Advances in Heterocyclic Chemistry, vol. 82, 99 pages.
Wang, X., et al., "A cationic gemini surfactant as effective inhibitor for mild steel in HCI solutions", Corrosion Science, 2010, 52, pp. 1268-1276.
Yurchenko, R.I. et al., "Comparative Effect of N-Decyl and N-Phenacylmethylpyridinium Bromides in Acid Corrosion of Steel", Russian Journal of Applied Chemistry, 2011, 84(11), pp. 2008-2010.
Yurchenko, R.I. et al., "Inhibiting Action of 1-Phenacylmethyl-2-R-Quinolinium Bromides at Steel Acid Corrosion", Russian Journal of Applied Chemistry, 2011, 84(11), pp. 2011-2012.
Ferreira, E. S. et al., "Evaluation of the inhibitor effect of L-ascorbic acid on the corrosion of mild steel", Materials Chemistry and Physics, 2004, 83(1), pp. 129-134.
Al-Taq, A. A. et al., "Inhibition Performance of a New Series of Mono-/Diamine-Based Corrosion Inhibitors for HCL Solutions", SPE 114807-PA, SPE Journal, 2009, 14(4), pp. 627-633.
Coppola, G. M. et al., Perhydroquinolylbenzamides as Novel Inhibitors of 11.beta.-Hydroxysteroid Dehydrogenase Type 1, Journal of Medicinal Chemistry, American Chemistry Society, 48 (21), 17 pages.
Schleimer, M. et al., "Enantiomer separation by high-performance liquid chromatography on polysiloxane-based chiral stationary phases", Journal of Chromatography A, 1994, 679(1), pp. 23-34.
Pirkle, W. H. et al., "An Improved Chiral Stationary Phase for the Facile Separation of Enantiomers", Journal of chromatography A, 1988, 441(20), pp. 311-322.
Pirkle, W. H. et al., "Chromatographic Separation of the Enantiomers of N-Acylated Heterocyclic Amines", Journal of Organic Chemistry, American Chemical Society, US, 1984, pp. 2504-2506.

Combined Search and Exam Report Under Sections 17 and 18(3) of UK Patent Application No. 1518417.9, dated May 9, 2016, 8 pages.
International Preliminary Report on Patentability of International Patent Application No. PCT/US2016/057259, dated May 3, 2018, 9 pages.
Supplementary Search Report of European Patent Application No. 16858033.0, dated Sep. 12, 2019, 12 pages.
Search Report and Written Opinion of International Patent Application No. PCT/US2015/056144, dated Dec. 23, 2015, 11 pages.
Search Report under Section 17.5 for UK Patent Application Serial No. GB142156.8, dated Feb. 18, 2015, 5 pages.
Supplementary Partial Search Report of European Patent Application No. 15864760.2, dated Jul. 2, 2018, 13 pages.
Search Report and Exam of European Patent Application No. 15864760.2, dated Nov. 19, 2018, 14 pages.
International Preliminary Report on Patentability of International Patent Application No. PCT/US2015/056144, dated Jun. 15, 2017, 8 pages.
Notice of Allowance in U.S. Appl. No. 15/533,315, dated Sep. 23, 2019, 19 pages.
International Preliminary Report on Patentability of International Patent Application No. PCT/US2015/056134, dated Oct. 17, 2017, 7 pages.
Office Action in U.S. Appl. No. 15/566,529, dated Oct. 11, 2018, 15 pages.
Combined Search and Examination Report under Sections 17 and 18(3) of GB Patent Application No. 1506217.7, dated Jan. 29, 2016, 6 pages.
Search Report and Written Opinion of International Patent Application No. PCT/US2015/056134, dated Dec. 7, 2015, 12 pages.
Office Action in U.S. Appl. No. 15/566,529, dated Apr. 11, 2019, 11 pages.
Frenier, W. W., "Corrosion, Passivation, and Inhibition", in Technology for Chemical Cleaning of Industrial Equipment, NACE International, Houston, Texas, 2001, pp. 51-91.
Exam Report in UK Patent Application No. 1518417.9, dated Apr. 7, 2020, 4 pages.

\* cited by examiner

CORROSION INHIBITION

BACKGROUND

There are numerous circumstances where it is desired to protect metal, notably steel or an alloy steel, from corrosion. These include the protection of steel used in a subterranean borehole to access a hydrocarbon reservoir and, more particularly but not by way of limitation the protection of steel exposed to a corrosive aqueous acidic liquid, such as when steel tubing is used to convey a flow of acidic aqueous liquid.

One industry which has a need for protection of steel against corrosion is oil and gas exploration and production. Steel tubulars used in a borehole may be exposed to corrosive conditions and so may steel pipelines used to carry produced oil and gas. In the oil and gas industry exposure to acidic solution may result from deliberate use of acid in an oilfield operation.

The technique of matrix acidizing, in which the producing formation is treated with acid to stimulate production, involves deliberate exposure of borehole steel to acid. This operation may be performed with coiled tubing, which is run into a borehole and then used to convey acid down the borehole to the formation. When the matrix acidizing operation comes to an end, the steel casing in the borehole and the exterior of the coiled tubing can be exposed to so-called unspent acid flowing back with formation fluids that flow back towards the surface.

Steel may be protected against corrosion by contacting the steel with an organic corrosion inhibitor. These organic inhibitors adsorb on the metal surface. Adsorbed inhibitor(s) may influence the rate of corrosion by one or more of several mechanisms: (i) by forming a physical barrier film which restricts the diffusion of species to/from the metal surface, (ii) by blocking anodic and/or cathodic reaction sites directly, (iii) by interacting with corrosion reaction intermediates adsorbed on the surface and (iv) by influencing the electrical double layer that forms at the metal/solution interface.

Adsorption may comprise physi-sorption which is the result of electrostatic attractive forces between inhibiting organic ions or dipoles and the electrically charged surface of the metal. The surface charge of the metal is due to the electric field at the outer Helmholtz plane of the electrical double layer existing at the metal/solution interface.

Another possibility is that adsorption is by chemi-sorption, which takes place more slowly than electrostatic adsorption and with a higher activation energy. Chemi-sorption involves electron transfer from electron-rich sites within the structure of the inhibitor molecule(s) to vacant low energy orbitals in the metal. Typically, such electron-rich sites within an inhibitor molecule are heteroatoms with lone pair(s) of electrons or are multiple bonds and aromatic rings so that covalent bonds have electrons in π-orbitals. Because activation energy is required, to bring about chemi-sorption, the extent of chemi-sorption and therefore the efficacy of corrosion inhibition may increase with temperature.

Aromatic nitrogen salts have been extensively used as corrosion inhibitors for mineral acids. Examples are n-alkyl pyridinium halides, n-alkylbenzylpyridinium halides, n-alkylisoquinolinium halides and n-alkylbenzylquinolinium halides. These compounds contain a cationic pyridinium or quinolinium group.

Schmitt, G. and Bedbur, K., in "Investigations on structural and electronic effects in acid corrosion inhibitors by AC impedance", Werkstoffe and Korrosion, v36 (1985), 273-278, compared several pyridinium and quinolinium derivatives on pure iron and steel in deaerated 10% hydrochloric acid and concluded that the best performance was given by naphthylmethylquinolinium chloride (NMQCl). Frenier, W. W., in "Acidizing fluids used to stimulate high temperature wells can be inhibited using organic chemicals", Society of Petroleum Engineers (SPE) paper 18468, presented at the SPE International Symposium on Oilfield Chemistry, 8-10 February, 1989, compared the acid corrosion inhibitor performance of various pyridinium and quinolinium compounds on carbon steel (N80) and the alloy 13Cr. Of all the compounds studied, NMQCl showed the best performance on N80 at 250° F. (125° C.); at this temperature, the test solutions contained 0.03 mol/L pyridinium or quinolinium inhibitor and 10 g/L phenyl ketone in 15 wt % or 28 wt % HCl. The superior performance of NMQCl was confirmed in further tests at 300° F. (149° C.) and 350° F. (177° C.).

Corrosion inhibitors may be marketed as a mixture containing materials which inhibit corrosion together with so-called "intensifier" materials which enhance the inhibition of corrosion in various circumstances, even though these other materials do not function as corrosion inhibitors (or are less efficacious) if used alone. A number of materials have been found to act as intensifiers, including formic acid, methyl formate, potassium iodide and salts of copper, antimony and bismuth.

It is generally desirable to minimise corrosion and therefore desirable that a corrosion inhibitor should be effective. In some circumstances, it is also desirable to minimise the amount of corrosion inhibitor which is included in the corrosive solution, either on grounds of cost or because of apprehension that it will cause problems when the corrosive solution is used or further treated. Thus there is a desire for corrosion inhibitors which are effective at low concentration in the corrosive solution taking into account that all the exposed metal/alloy surfaces should be effectively protected.

SUMMARY

This summary is provided to introduce a selection of concepts that are further described below. This summary is not intended to be used as an aid in limiting the scope of the subject matter claimed.

A first aspect of the present disclosure is a corrosion inhibiting compound with a general structure A-B, wherein A comprises a heterocyclic ring system comprising a plurality of cyclic Carbon atoms and at least one cyclic Nitrogen atom, wherein the at least one cyclic Nitrogen atom is neutral under neutral conditions and protonatable under acidic conditions; and wherein B comprises at least two unsaturated Carbon atoms.

Sub-structure A comprises at least one cyclic Nitrogen atom which is neutral under neutral and alkaline solutions and protonatable under acidic solutions. Preferably, A does not comprise any Nitrogen atoms which are positively charged under neutral conditions. The inhibitors of the present disclosure are therefore insoluble under neutral or alkaline conditions, and become protonated and thus soluble in acidic solutions.

Their solubility in acidic solutions allows them to act as an acid corrosion inhibitor in acidic solutions. As shown below, the protonated inhibitors of the present disclosure perform better than or at least comparable to prior art inhibitors.

Meanwhile, the inhibitors of the present disclosure are insoluble at neutral or alkaline pH due to de-protonation. This reduces their toxicity level especially in neutral and alkaline solutions, which is good for the environment.

These features allow them to work as an efficient acid inhibitor in acidic solutions where an acid inhibitor is needed due to acidic corrosion on metal surfaces and allow them to come out of the solution thereby reducing their toxicity level to zero in neutral and alkaline solutions where an acid inhibitor is not needed.

For example, in the oil industry and in matrix acidizing operations they would work as efficient acid inhibitors downhole, and then they would become insoluble in spent acid and formation brine when fluids flow back to the surface resulting in zero aquatic toxicity.

The Chemical composition of substructure A is different from that of substructure B. Optionally, B does not comprise any cyclic Nitrogen atoms. B may comprise a homocyclic ring system. Alternatively, B may comprise a polymerisable group comprising at least one double or triple bond.

B is connected to one of the cyclic atoms of substructure A. B may be connected to a cyclic Carbon atom or a cyclic Nitrogen atom of the heterocyclic ring system of A.

A and B may be connected via a linking Nitrogen atom, the linking Nitrogen atom being one of the at least one cyclic Nitrogen atom in A.

If A comprises only one cyclic Nitrogen atom, A and B may be connected via this Nitrogen atom. In other words, this only one Nitrogen atom may be the linking Nitrogen atom.

If A comprises more than one cyclic Nitrogen atoms which are not permanently positively charged but which protonate in acidic solutions to provide solubility and acid corrosion inhibition, then the linking Nitrogen may be one of the more than one cyclic Nitrogen atoms.

A and B may be connected directly via a covalent bond. Alternatively, the corrosion inhibiting compound may have a general structure A-X-B where sub-structure A is a heterocyclic ring system, sub-structure B is comprises at least two unsaturated Carbon atoms and X is a linkage between A and B.

X may comprise one or more Carbon atoms. In some embodiments X may be a Carbon chain, which may be linear or branched; saturated or unsaturated. In other embodiments, X may also comprise one or more other atoms such as Nitrogen or Oxygen, either along the main chain of the structure of X, or as part of a branch.

In some embodiments, X is methylene.

A may comprise a plurality of rings such as one or two or three rings. The rings may be separate or fused. A may be fully saturated, partially unsaturated, or fully unsaturated. In particular, one or more or all of the rings may be aromatic, while one or more or all of the rings may be fully saturated.

In some embodiments, sub-structure A comprises at least two non-aromatic cyclic carbons. This goes against prior art teaching and reduces the amount of aromaticity. However, these molecules showed comparable performance as acid corrosion inhibitors.

Optionally, a cyclic Carbon atom in A is directly connected to the linking Nitrogen atom in A and the cyclic Carbon atom is saturated.

A may comprise one or more six membered rings and/or one or more five membered rings.

In some embodiments, A is tetrahydroquinoline.

Optionally, B comprises a homocyclic ring system comprising a plurality of cyclic Carbon atoms. B may comprise two or three fused rings. Such ring systems may be fully saturated, partially saturated, or fully unsaturated.

B may comprise a plurality of aromatic rings. For example, B may be naphthyl.

Alternatively, B may comprise a non-cyclic structure comprising at least two unsaturated Carbon atoms. For example, B may comprise a polymerisable group.

In addition, a polymerisable group may be attached to A and/or B, directly or indirectly.

A second aspect of the present disclosure is a method of inhibiting corrosion of a metal surface exposed to an aqueous solution comprising including in the solution a corrosion inhibiting compound as specified above.

A third aspect of the present disclosure is the use of a corrosion inhibiting compound as specified above to minimize corrosion of metal surfaces in acidic solutions.

A fourth aspect of the present disclosure is the use of a corrosion inhibiting compound as specified above in oil and gas industry.

A fifth aspect of the present disclosure is the use of a corrosion inhibiting compound as specified above in water industry, geothermal energy, $CO_2$ sequestration, Carbon services, or nuclear industry.

DETAILED DESCRIPTION

Figure 1:
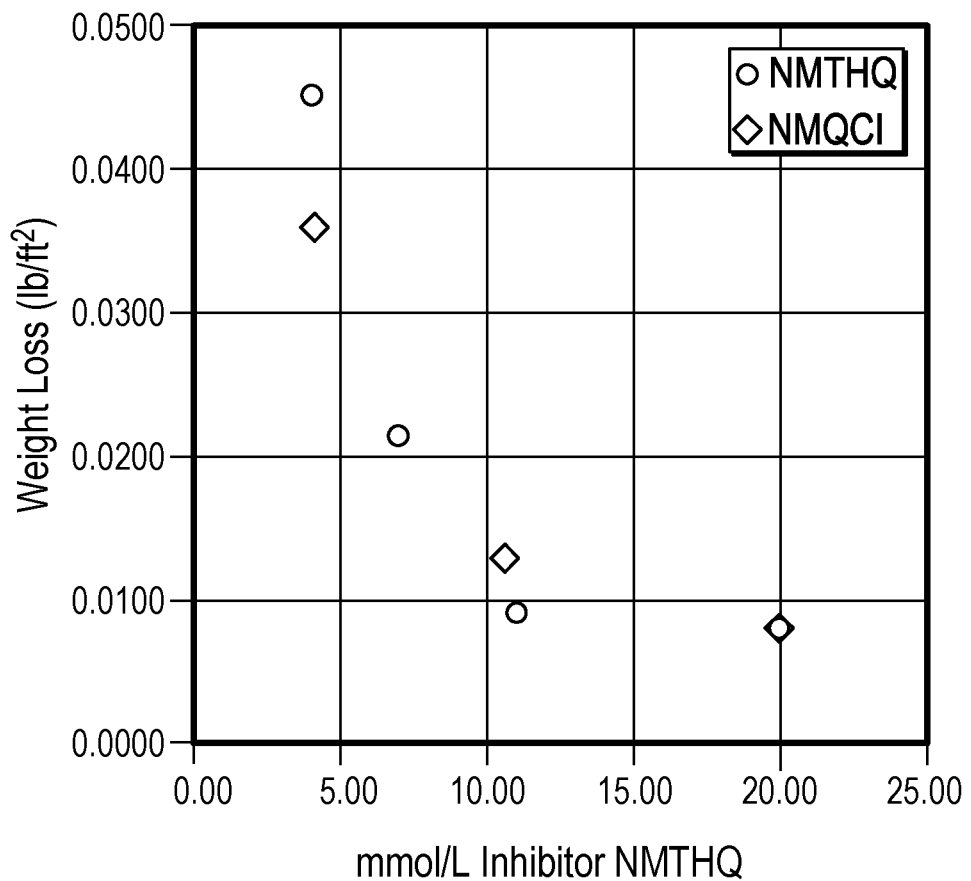
FIG. 1 is a graph showing weight loss results in example 1 below using duplex stainless steel 22Cr125.

The current use of corrosion inhibitor products involves the addition of a certain concentration or dosage of the inhibitor product to a corrosive fluid. The physico-chemical properties of the corrosive fluids vary according to the application and prevailing wellbore and reservoir conditions. The corrosive fluid may comprise (i) a treatment fluid injected from surface via the wellbore into the formation such as a matrix acidizing fluid or an acid fracturing fluid, (ii) a fluid injected into the reservoir to improve or enhance the recovery of hydrocarbons (IOR/EOR applications) or (iii) produced fluids (multiphase) flowing from the reservoir to surface via the wellbore. Such injection and production operations expose a broad range of tubing, casing and downhole equipment to a wide range of different corrosive fluid compositions. This tubing, casing and downhole equipment is largely composed of carbon steels and low and high alloys. Exposure times vary from a few hours in the case of low volume matrix acidizing stimulation treatments to months or years in the case of reservoir conformance fluids and produced fluids. It is known that the efficiency of corrosion inhibitor products depends on the composition and microstructure of the metal or alloy substrate. Details pertaining to any given application dictate the nature of the exposed metal/alloy type(s), the composition and properties of the corrosive fluid, the range of exposure times and the prevailing physico-chemical conditions including temperature, pressure, oxygen concentration and the presence and concentration of acid gases, $CO_2$ and $H_2S$.

For any given application, laboratory corrosion tests on suitable test coupons of the relevant metal and alloy types are used to identify a suitable inhibitor chemistry/product and the dosage required to reduce the rate of corrosion to an "acceptable" level. In general, this "acceptable" level is defined by (i) a maximum generalized corrosion rate, i.e. a maximum cumulative weight loss per unit area recorded after a relevant exposure period and (ii) a maximum degree of localized corrosion as specified by a maximum "pitting index". Typically, the minimum dosage of the corrosion inhibitor used in the application is the dosage required to achieve "acceptable" levels of generalized and localized corrosion. Such "acceptable" levels of corrosion are application-specific.

In matrix acidizing, the test coupons are usually fabricated from various coiled tubing and wellbore casing materials with a surface area of 25-30 $cm^2$. In this case, the typical "acceptable" level of generalized corrosion is ≤0.05 $lb/ft^2$, and preferably ≤0.01 $lb/ft^2$, as determined after an exposure period matched to that which will be encountered in the application. Typically, the cumulative weight loss and pitting index (PI) of coiled tubing test coupons is determined after exposure periods in the range 3-48 hours. Typically, the "acceptable" level of localized corrosion is defined by a maximum PI=2 and, more preferably, by the absence of any pits (PI=0).

In produced fluid applications, a range of different laboratory tests are performed and typical "acceptable" corrosion rates as determined by linear polarization resistance (LPR) or electrochemical impedance spectroscopy (EIS) are millimetres/year (as determined by tests lasting 10-30 days).

LPR measurement was first proposed by M Stern and A L Geary in "Electrochemical Polarization: I. A Theoretical Analysis of the Shape of Polarization Curves" in J. Electrochem. Soc. Vol 104 pp 56-63 (1957) and followed by Stern: "A Method For Determining Corrosion Rates From Linear Polarization Data" in Corrosion, Vol. 14, No. 9, 1958, pp 440-444. In such tests a piece of the steel is used as an electrode and this electrode may be kept moving as a rotating disc, cylinder or cage to simulate flow of the corrosive solution over the steel.

EIS can be used to monitor the corrosion rate of a system. The parameter of interest is the charge transfer resistance, $R_{ct}$, which can be thought of the 'resistance' to corrosion. A metal test piece is used as the working electrode in a three-electrode electrochemical cell with the corrosive solution as electrolyte. Impedance data is obtained by applying a small alternating voltage to the working electrode and measuring the resulting current to obtain a value of impedance. This is done at a range of frequencies. Then, in order to extract the parameter of interest, the metal/inhibitor/electrolyte interfaces are modelled as an electrical equivalent circuit and the theoretical impedance is fitted to the data.

The extent to which such laboratory tests simulate the physico-chemical conditions prevailing in a given application is a topic which has been the subject of many publications. Several physico-chemical variables (temperature, pressure, oxygen concentration and the presence and concentration of acid gases, $CO_2$ and $H_2S$) are well controlled in typical laboratory tests. However, it is also desirable to test inhibition efficiency under dynamic flow conditions preferably matched to those which will be encountered during field treatments. It is thus important to design tests which also consider several other critical variables; these include: realistic flow conditions, i.e. representative Reynold's numbers and wall shear stresses for corrosive fluid flow in contact with the internal or external surface of relevant tubing or internal surface of casing; realistic temperature history conditions, e.g. heat-up profiles for injected fluids; realistic presence and concentration of solids in produced fluids, e.g. reservoir sanding conditions, and associated erosion-corrosion conditions including a representative range of solid particle impingement velocities; and/or realistic presence, concentration and composition of non-aqueous phases and other additives, e.g. gas hydrate inhibitors, asphaltene inhibitors and demulsifiers, in production chemical mixtures.

The present disclosure is concerned with a corrosion inhibition compound with a general structure A-B or A-X-B. This disclosure is also concerned with the use of such compounds as corrosion inhibitors in a corrosive solution, in particular in a corrosive acidic aqueous solution. Surfaces to be protected from corrosion will ordinarily be metallic and the metal may be an alloy. In some embodiments, such a compound is included in an inhibitor composition which is used to protect a system in which there are a plurality of metals which come into contact with corrosive aqueous acidic liquid. The metal surfaces to be protected may be steel and the steel may be a single phase steel or a duplex alloy steel. An alloy steel may contain nickel, chromium, molybdenum and possibly other alloying metals. The metals may be located within a subterranean borehole.

Substructure A

Sub-structure A comprises a heterocyclic ring system having a plurality of cyclic Carbon atoms and at least one cyclic Nitrogen atom. Optionally, at least two of the plurality of cyclic Carbon atoms are saturated. In other words, sub-structure A may comprise at least two non-aromatic carbons such that its overall H/C ratio is unity or greater. Alternatively, the heterocyclic ring system of substructure A may be fully unsaturated or fully saturated.

The heterocyclic ring system of Sub-structure A comprises one or more cyclic Nitrogen atoms which are not positively charged but which protonate in acidic solutions to provide solubility. Thus, for example, 1-(naphthyl methyl 1,2,3,4-tetrahydroquinoline (NMHQ) protonates in acid solution as shown below:

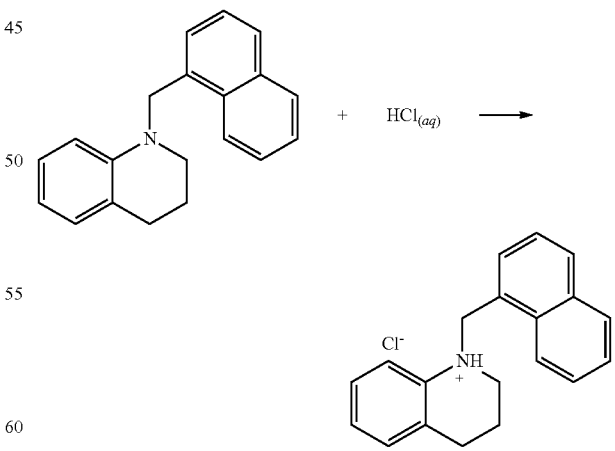

The heterocyclic ring system of Sub-structure A may contain one cyclic Nitrogen atom that's neutral under neutral conditions. The heterocyclic ring system may contain two or three fused rings. Each ring may be made of six cyclic Carbon atoms, for example:

1,2,3,4-tetrahydro-quinoline   1,2,3,4-tetrahydro-iso-quinoline

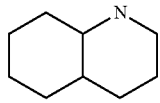 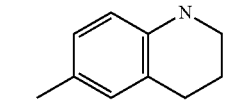

decahydro-quinoline   6-methyl- 1,2,3,4-tetrahydro-quinoline

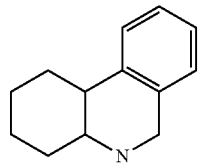

1,2,3,4,4a,5,6,10b-octahydrophenanthridine

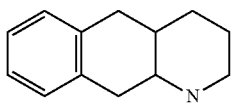

1,2,3,4,4a,5,10,10a-octahydrobenzoquinoline

The heterocyclic ring system of Sub-structure A may contain one cyclic Nitrogen atom that's neutral under neutral conditions. The heterocyclic ring system may contain a plurality of fused rings. Some of the rings may be made of five cyclic Carbon atoms, for example:

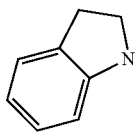 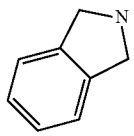

indoline   iso-indoline

The heterocyclic ring system may contain a single ring containing one cyclic Nitrogen atom that's neutral under neutral conditions. The ring may be made of five or six cyclic Carbon atoms, for example:

  

2,3-dihydro-1H-pyrrole   pyrrolidine   Piperidine

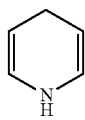

Dihydropyridine

The heterocyclic ring system may contain more than one cyclic Nitrogen atom that's neutral under neutral conditions. The ring system may contain a single ring or a plurality of fused rings, for example:

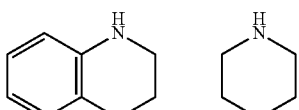

1,2,3,4-tetrahydroquinoxaline   piperazine

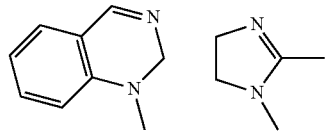

Dihydroquinazoline   Imidazoline

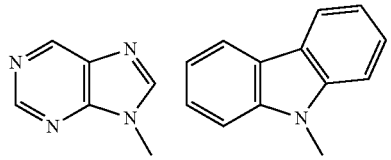

Purine   Carbazole

The heterocyclic ring system may also contain another hetero atom in addition to one or more cyclic Nitrogen atom that's neutral under neutral conditions, for example:

 

morpholine   thiomorpholine

Substructure B

Sub-structure B comprises at least two unsaturated Carbon atoms. B may comprise a homocyclic ring system having a plurality of cyclic Carbon atoms. The ring system may comprise two or three fused or linked rings. The rings may be aromatic, for example:

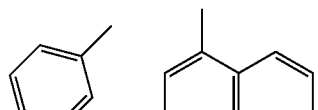

Benzyl   Naphthyl

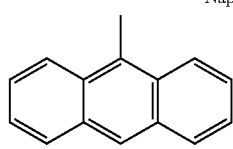

Anthracenyl

The homocyclic ring system of B may comprise saturated Carbon atoms. For example:

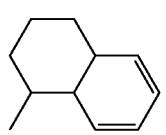

In summary, preferred substructure B include benzyl, naphthyl, naphthyl methyl, fused aromatic right structures or mixed aliphatic and aromatic ring structures.

Sub-structure B may comprise one or more polymerisable groups containing at least one double or triple bonded Carbon atom, for example —C(OH)—C≡CH, C≡C—, and/or —C≡N. Such a polymerisable group is intended to polymerise with other polymerisable groups after adsorption onto a metal surface, and this enables the molecules to combine together as a protective film which enhances acid corrosion inhibition.

Linking Structure X

Sub-structure A and sub-structure B can be connected directly via a covalent bond. An example of such an acid corrosion inhibitor is as follows:

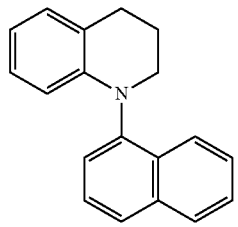

1-(naphthalen-1-yl)-1,2,3,4-tetrahydroquinoline

Alternatively, A and B can be connected via a linking group X. The general structure of the acid corrosion inhibitor becomes A-X-B.

The linking group X may be a saturated Carbon chain comprising one or two Carbon atoms. In principle, X can also be a longer Carbon chain, linear or branched, fully saturated or partially unsaturated, aliphatic or aromatic.

Specific possibilities for a linking group X joining A and B are a saturated polymethylene chain

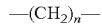

an unsaturated alkylene chain, i.e. a chain of aliphatic carbon atoms with at least one olefinic double bond in the chain such as

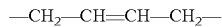

and a mixed aliphatic aromatic chain in which two aliphatic groups are connected by an aromatic ring, such as

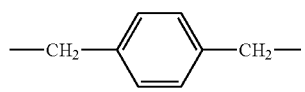

Furthermore, the linking group may also comprise one or more hetero atoms either attached to the main chain of X or as part of the main chain of X, as is the case in the below examples:

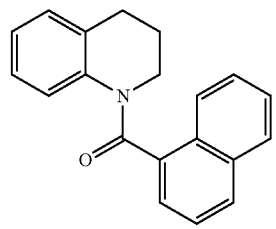

(3,4-dihydroquinolin-1(2H)-yl)
(naphthalen-1-yl)methanone

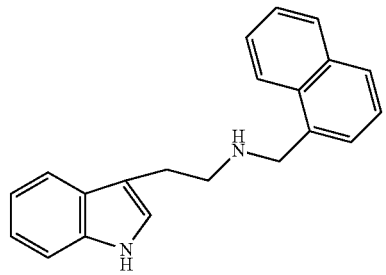

2-(1H-Indol-3-yl)-N-(naphthalene-1-ylmethyl)ethan-1-amine (3)

A comprises a heterocyclic ring system having at least one cyclic Nitrogen atom. A and B may be linked directly or indirectly via one of the at least one cyclic Nitrogen atom of A. This is not essential. Optionally, A can be linked via one of its constituent Carbon atoms.

Additional Attachments

In addition, one or more of the rings in sub-structure A and/or sub-structure B may have one or more additional groups attached which are intended to enhance adsorption onto a metal surface or provide an additional function:

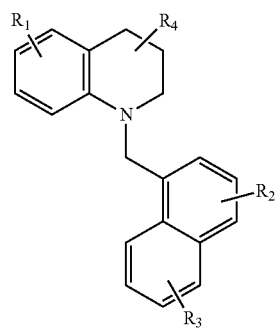

For instance, the substructure A below, 1,2,3,4-tetrahydroquinoline, could have an additional polymerisable group attached to one of its rings, as illustrated below:

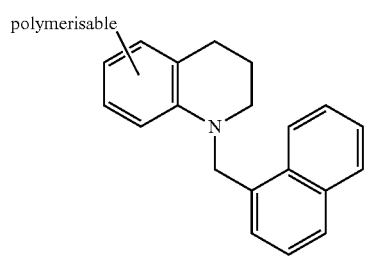

Alternatively or additionally, other groups could be substituents on substructure A and/or B. These may enhance chemisorption.

EXPERIMENTS

Experiments were carried out with coupons of the following steels:
22Cr125 also designated 2205, a duplex alloy steel which is an iron-chromium-nickel-molybdenum alloy, used (among other things) to fabricate casing.
HS80™ (TradeMark of TENARIS), a low carbon steel used to fabricate coiled tubing.
N80, a medium carbon steel used to fabricate borehole casing.
13Cr80, an alloy steel containing 13 wt % chromium without nickel, also used to fabricate borehole casing.

Example 1: NMTHQ

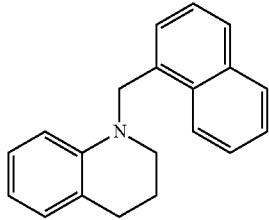

1-(Naphthalen-1-ylmethyl-1,2,3,4-tetrahydroquinoline (NMTHQ)

NMTHQ Synthesis:

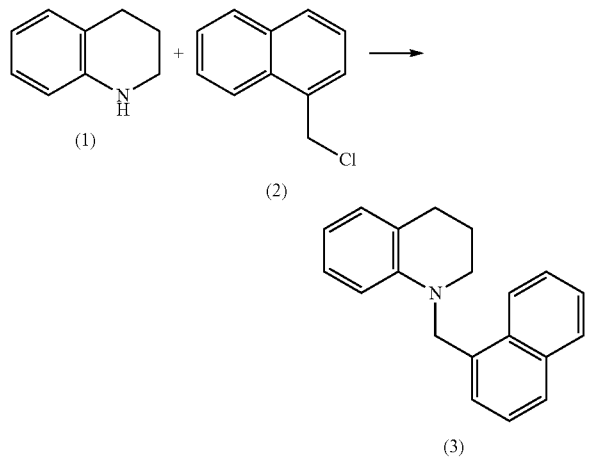

1,2,3,4-Tetrahydroquinoline (1) (9.94 g, 74.6 mmol), 1-(chloromethyl)naphthalene (2) (11.87 g, 67.2 mmol) and potassium carbonate (22 g, 159 mmol) were heated in dimethylformamide at 85° C. for 19 hr. The suspension was cooled, the solid filtered and washed with dimethylformamide. Diethyl ether and water were added to the filtrate; the organic phase was removed, extracted with water, evaporated and the resultant solid washed with diethyl ether to give 1-(naphthalen-1-ylmethyl-1,2,3,4-tetrahydroquinoline (3), 14.3 g (78% yield) which was used without further purification.

Corrosion Inhibition Efficiency Tests on Metal Surfaces
(1) Metal Type: Duplex Stainless Steel 22Cr125 Casing (2205 b6); 4 mol/L HCl, T=80° C., 3 Hours Exposure

| Concentration NMTHQ (273.37 g/mol) | | Weight Loss | | |
| --- | --- | --- | --- | --- |
| Wt % | mmol/L | lb/ft$^2$ | kg/m$^2$ | Pitting Index |
| 0.11 | 4.02 | 0.0453 | 0.2212 | 4 |
| 0.1913 | 7.00 | 0.0216 | 0.1055 | 3 |
| 0.30 | 10.97 | 0.0091 | 0.0444 | 0 |
| 0.547 | 20.01 | 0.0081 | 0.0395 | 0 |

| Concn. 1,2,3,4-tetrahydroquinoline | | Weight Loss | | |
| --- | --- | --- | --- | --- |
| Wt % | mmol/L | lb/ft2 | kg/m2 | Pitting Index |
| 0.1465 | 11.00 | 0.6383 | 3.1165 | 6 |

| Concentration NMQCl (305.8 g/mol) | | Weight Loss | | |
| --- | --- | --- | --- | --- |
| Wt % | mmol/L | lb/ft$^2$ | kg/m$^2$ | Pitting Index |
| 0.123 | 4.03 | 0.0360 | 0.1758 | 4 |
| 0.322 | 10.54 | 0.0131 | 0.0640 | 0 |
| 0.612 | 20.00 | 0.0081 | 0.0395 | 0 |

| Concn. Quinoline | | Weight Loss | | |
| --- | --- | --- | --- | --- |
| Wt % | mmol/L | lb/ft2 | Wt % | Pitting Index |
| 0.1421 | 11.00 | 0.4517 | 0.1465 | 6 |

The above data and graph in FIG. 1 show that when compared at equivalent molar concentrations, the inhibition performance of NMTHQ is very similar to the known acid corrosion inhibitor NMQCl. Data showing the relatively poor acid inhibition performance of 1,2,3,4-tetrahydroquinoline and quinoline are also shown for comparison.

It is also noted that when compared at equivalent weight percentages, NMTHQ is more efficient due to its lower molecular weight (NMTHQ 273.37 g/mol; NMQCl 305.8 g/mol).

In addition, as detailed below, relative to NMQCl, a significant additional performance benefit given by the use of NMTHQ is that it deprotonates under near neutral pH conditions leading to negligible solubility and aquatic toxicity. Thus, the aquatic toxicity due to any NMTHQ present in acidizing flowback fluids is negligible.

(2) Metal Type: N80 Casing, 4 mol/L HCl, T=80° C., 3 Hours Exposure

| Concentration NMTHQ (273.37 g/mol) | | Weight Loss | | |
| --- | --- | --- | --- | --- |
| Wt % | mmol/L | lb/ft$^2$ | kg/m$^2$ | Pitting Index |
| 0.3000 | 10.97 | 0.0033 | 0.0161 | 0 |
| 0.3013 | 11.02 | 0.0052 | 0.0254 | 0 |
| 0.3017 | 11.04 | 0.0062 | 0.0303 | 0 |
| 0.2065 | 7.55 | 0.0087 | 0.0425 | 2 |
| 0.1368 | 5.00 | 0.0174 | 0.0850 | 3 |

| Concentration NMQCl (305.8 g/mol) | | Weight Loss | | |
| --- | --- | --- | --- | --- |
| Wt % | mmol/L | lb/ft$^2$ | kg/m$^2$ | Pitting Index |
| 0.3386 | 11.07 | 0.0085 | 0.0415 | 0 |
| 0.3394 | 11.10 | 0.0055 | 0.0269 | 0 |
| 0.1534 | 5.02 | 0.0129 | 0.0630 | 3 |

The N80 data show that when compared at equivalent molar concentrations, the inhibition performance of NMTHQ is similar to the known acid corrosion inhibitor NMQCl.

It is noted that when compared at equivalent weight percentages, NMTHQ is more efficient due to its lower molecular weight (NMTHQ 273.37 g/mol; NMQCl 305.8 g/mol).

(3) Metal Type: HS80 Coiled Tubing; 4 mol/L HCl, T=80° C., 3 Hours Exposure

| Concentration NMTHQ (273.37 g/mol) | | Weight Loss | | |
|---|---|---|---|---|
| Wt % | mmol/L | lb/ft$^2$ | kg/m$^2$ | Pitting Index |
| 0.0055 | 0.20 | 0.4222 | 2.0614 | 5 |
| 0.0273 | 1.00 | 0.1235 | 0.6030 | 2 |
| 0.11 | 4.02 | 0.0225 | 0.1099 | 0 |
| 0.1366 | 5.00 | 0.0193 | 0.0942 | 0 |
| 0.192 | 7.02 | 0.0070 | 0.0342 | 0 |

| Concentration NMQCl (305.8 g/mol) | | Weight Loss | | |
|---|---|---|---|---|
| Wt % | mmol/L | lb/ft$^2$ | kg/m$^2$ | Pitting Index |
| 0.0015 | 0.05 | 0.4411 | 2.1536 | 5 |
| 0.06225 | 2.04 | 0.0445 | 0.2173 | 0 |
| 0.1531 | 5.01 | 0.0165 | 0.0806 | 0 |
| 0.3366 | 11.01 | 0.0010 | 0.0049 | 0 |

Figure 2:
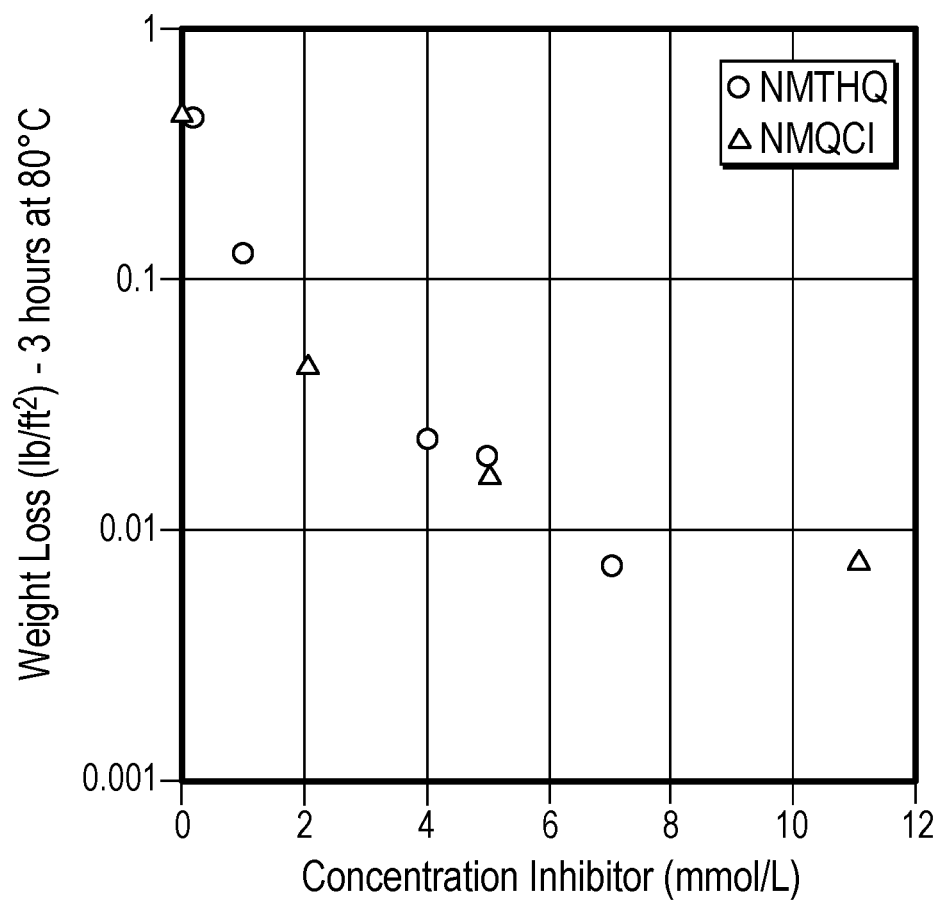
FIG. 2 is a graph showing weight loss results in example 1 below using HS80 coiled tubing.

The above data are shown in a plotted graph in FIG. 2.

The HS80 data show that when compared at equivalent molar concentrations, the inhibition performance of NMTHQ is similar to the known acid corrosion inhibitor, NMQCl.

It is again noted that when compared at equivalent weight percentages, NMTHQ is more efficient due to its lower molecular weight (NMTHQ 273.37 g/mol; NMQCl 305.8 g/mol).

(4) Metal Type: 13Cr80 Casing Material; 4 mol/L HCl, T=80° C., 3 Hours Exposure

| Concentration NMTHQ (273.37 g/mol) | | Weight Loss | | |
|---|---|---|---|---|
| Wt % | mmol/L | lb/ft$^2$ | kg/m$^2$ | Pitting Index |
| 0.3000 | 10.97 | 0.0018 | 0.0088 | 0 |
| 0.1367 | 5.00 | 0.0366 | 0.1787 | 4 |

| Concentration NMQCl (305.8 g/mol) | | Weight Loss | | |
|---|---|---|---|---|
| Wt % | mmol/L | lb/ft$^2$ | kg/m$^2$ | Pitting Index |
| 0.3466 | 11.33 | 0.0124 | 0.0605 | 0 |
| 0.1545 | 5.05 | 0.0497 | 0.2427 | 5 |

Figure 3:
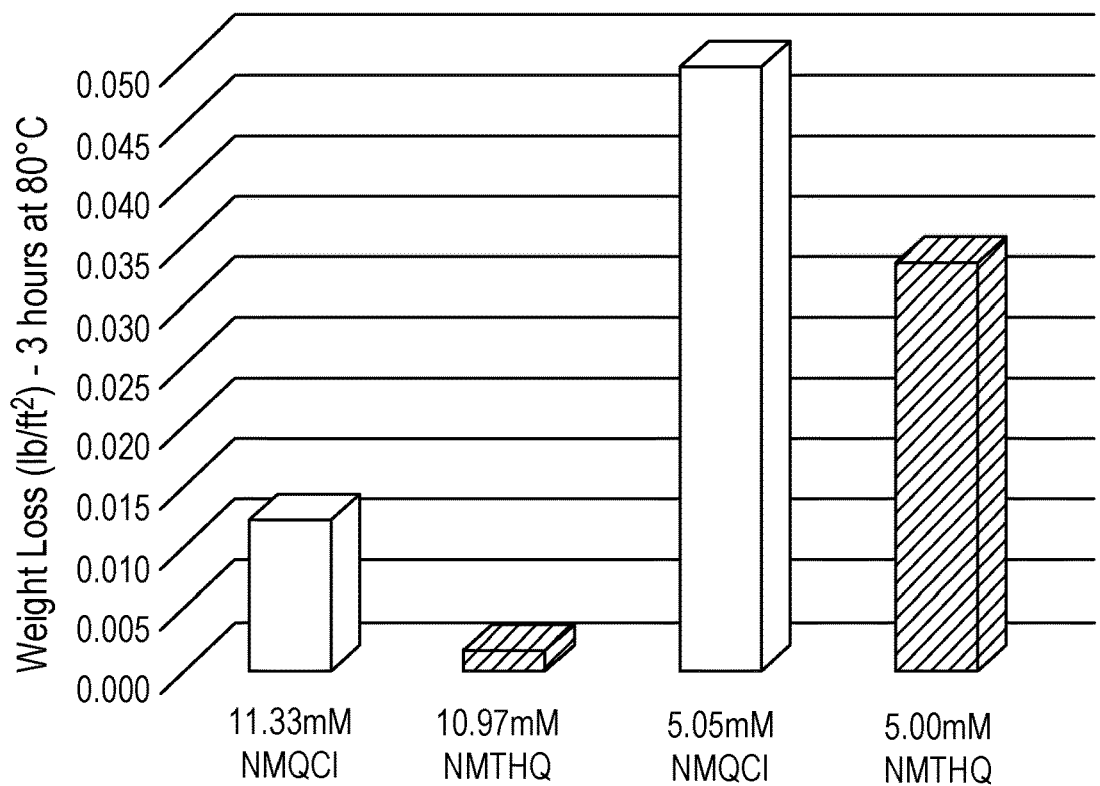
FIG. 3 is a bar chart showing weight loss results in example 1 below using 13Cr80 Casing Material.

The 13Cr80 data above and plotted graph in FIG. 3 show that when compared at equivalent molar concentrations, the inhibition performance of NMTHQ is superior to the known acid corrosion inhibitor, NMQCl.

(5) NMTHQ Performance in Presence of Potassium Iodide

| Metal type | Concentration NMTHQ (273.37 g/mol) | | Concn. KI | Weight Loss | | Pitting Index |
|---|---|---|---|---|---|---|
| | Wt % | mmol/L | mmol/L | lb/ft$^2$ | kg/m$^2$ | |
| 2205 (b6) | 0.11 | 4.02 | 0 | 0.0453 | 0.2212 | 4 |
| 2205 (b6) | 0.11 | 4.02 | 10 | 0.0048 | 0.0234 | 0 |
| 2205 (b5) | 0.1367 | 5.00 | 0 | 0.0242 | 0.1182 | 4 |
| 2205 (b5) | 0.1368 | 5.00 | 20 | 0.0022 | 0.0107 | 0 |
| 2205 (b5) | 0 | 0 | 10 | 0.2621 | 1.2800 | 5 |
| 2205 (b5) | 0 | 0 | 20 | 0.1326 | 0.6474 | 5 |
| HS80 | 0.1366 | 5.00 | 0 | 0.0193 | 0.0942 | 0 |
| HS80 | 0.1366 | 5.00 | 10 | 0.0022 | 0.0107 | 0 |
| HS80 | 0 | 0 | 10 | 0.1664 | 0.8124 | 2 |
| N80 | 0.1368 | 5.00 | 0 | 0.0174 | 0.0850 | 3 |
| N80 | 0.1389 | 5.08 | 10 | 0.0033 | 0.0161 | 0 |
| N80 | 0 | 0 | 10 | 0.1850 | 0.9032 | 5 |
| 13Cr80 | 0.1367 | 5.00 | 0 | 0.0366 | 0.1787 | 4 |
| 13Cr80 | 0.1382 | 5.06 | 10 | 0.0035 | 0.0171 | 0 |
| !3Cr80 | 0 | 0 | 10 | 0.7527 | 3.6750 | 5 |

The acid inhibition performance of NMTHQ is greatly enhanced by addition of adsorption intensifiers containing iodide. For example, as shown in the above table, for all four metal/alloy types, the performance of 4.0-5.7 mmol/L NMTHQ is enhanced by the addition of 5-20 mmol/L potassium iodide. Control experiments show relatively low inhibition efficiencies given by equivalent concentrations of potassium iodide in the absence of NMTHQ.

When the NMTHQ concentration is 4.0-5.1 mmol/L, the addition of 10 mM potassium iodide reduces the weight loss for 2205 (b6), HS80, N80 and 13Cr80 by the factors 9.4, 8.8, 5.3 and 10.5, respectively.

It is known that adsorption intensifiers such as potassium iodide greatly enhance the performance of various cationic acid corrosion inhibitors including NMQCl. The data shown in the above table are consistent with the presence of the protonated form of NMTHQ, i.e. species (B) shown in the below reaction, and its response to iodide.

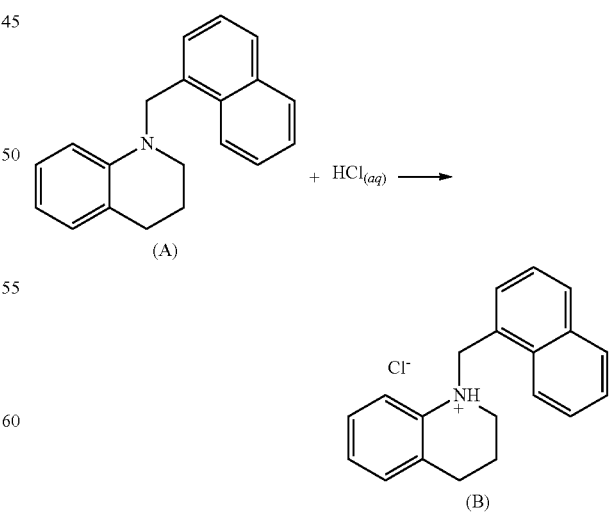

Adsorption of the protonated species (B) is enhanced by potassium iodide.

Example 2: NMTHisoQ

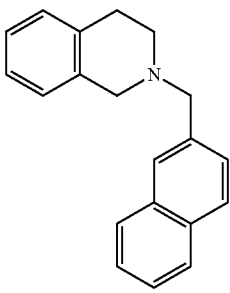

2-(Naphthalen-2-ylmethyl)-1,2,3,4-tetrahydroisoquinoline

The second example of this disclosure, NMTHisoQ, is an isomer of NMTHQ (example 1)

NMTisoQ Synthesis:

Similarly, NMTHisoQ is prepared by reaction of tetrahydro iso-quinoline (1) with 1-(chloromethyl)naphthalene (2):

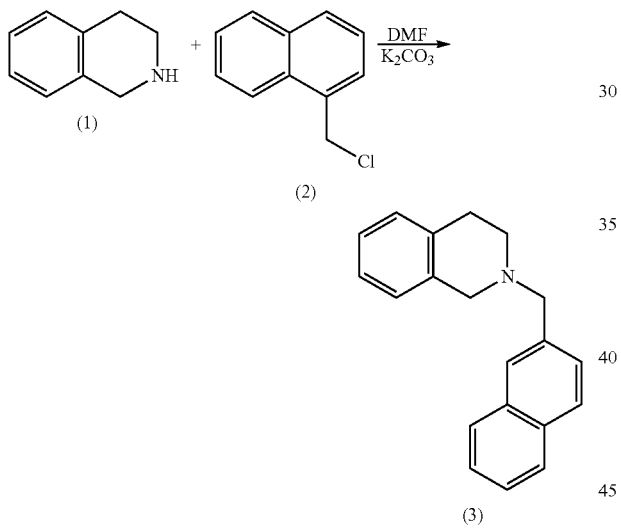

Corrosion Inhibition Efficiency Tests on Metal Surfaces

The acid inhibition performance of NMTHisoQ was evaluated for Duplex stainless steel 2205 casing immersed in 4 mol/L HCl, T=80° C., 3 hours exposure—the results are given below:

| Metal type | Concentration NMTHisoQ (273.37 g/mol) | | Concn. KI | Weight Loss | | Pitting |
| --- | --- | --- | --- | --- | --- | --- |
| | Wt % | mmol/L | mmol/L | lb/ft² | kg/m² | Index |
| 2205 (b5) | 0.1367 | 5.00 | 0 | 0.0239 | 0.1167 | 1 |
| 2205 (b5) | 0.1366 | 5.00 | 20 | 0.0025 | 0.0122 | 0 |
| 2205 (b5) | 0 | 0 | 20 | 0.1326 | 0.6474 | 5 |

As shown above, NMTHisoQ exhibits a high acid inhibition efficiency which, in the presence or absence of potassium iodide is similar to its isomer, NMTHQ.

Example 3: NMDHQ

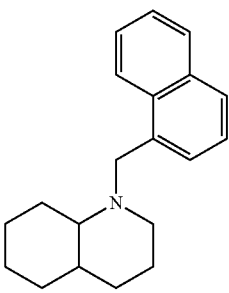

1-(Naphthalen-1-ylmethyl)decahydroquinoline

Relative to the structure of NMTHQ (example 1) and NMTHisoQ (example 2), NMDHQ incorporates additional hydrogen atoms leading to the presence of 9 saturated carbons in the quinoline sub-structure. As for NMTHQ and NMTHisoQ, NMDHQ converts to the protonated form under acid conditions—this reversible process leads to good acid solubility, good acid inhibition performance and insolubility and thus low toxicity under neutral pH conditions.

NMDHQ Synthesis:

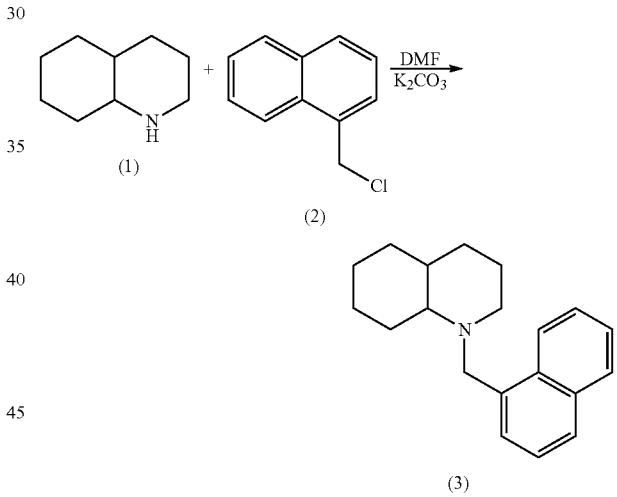

Decahydroquinoline comprising a mixture of cis and trans stereoisomers (1) (2.31 g, 8.27 mmol), 1-(chloromethyl)naphthalene (2) (2.64 g, 14.94 mmol) and potassium carbonate (4.95 g, 35.8 mmol) were added to dimethylformamide (21 ml) and heated at 90° C. for 18 hrs. The suspension was cooled, solid filtered and washed with dimethylformamide. Water was added to the filtrate and extracted with diethyl ether. The organic phase was backwashed with water, dried over sodium sulfate and the solvent removed. The residue was purified by column chromatography eluting with 0-5% ethyl acetate in hexane to give 1-(naphthalen-1-ylmethyl)decahydroquinoline (3), 3.64 g, (87% yield).

Corrosion Inhibition Efficiency Tests on Metal Surfaces

As shown by the data in the below table, NMDHQ is also an efficient acid corrosion inhibitor and its efficiency is enhanced by the presence of potassium iodide.

| | Concentration NMDHQ | | Concn. KI | Weight Loss | | Pitting |
|---|---|---|---|---|---|---|
| Metal type | Wt % | mmol/L | mmol/L | lb/ft² | kg/m² | Index |
| 2205 (b8) | 0.3088 | 11.05 | 0 | 0.0294 | 0.1435 | 1 |
| N80 | 0.3068 | 10.98 | 0 | 0.0099 | 0.0483 | 0 |
| 13Cr | 0.3094 | 11.07 | 0 | 0.0177 | 0.0864 | 2 |
| HS80 | 0.3061 | 10.95 | 0 | 0.0214 | 0.1045 | 2 |
| 2205 (b8) | 0.1414 | 5.0 | 10 | 0.0086 | 0.0420 | 0 |
| 2205 (b8) | 0.1414 | 5.0 | 20 | 0.0034 | 0.0166 | 0 |

Example 4: 4aR-8aS-NMDHQ

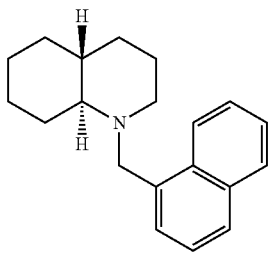

(4aR,8aS)-1-Naphthalen-1-ylmethyl)decahydroquinoline

4aR-8aS-NMDHQ is the trans stereoisomer of NMDHQ (example 3).

As described for NMTHQ, NMTHisoQ and NMDHQ, 4aR-8aS-NMDHQ converts to the protonated form under acid conditions—this reversible process leads to good acid solubility, good acid inhibition performance and insolubility and low toxicity under neutral pH conditions.

4aR-8aS-NMDHQ Synthesis:

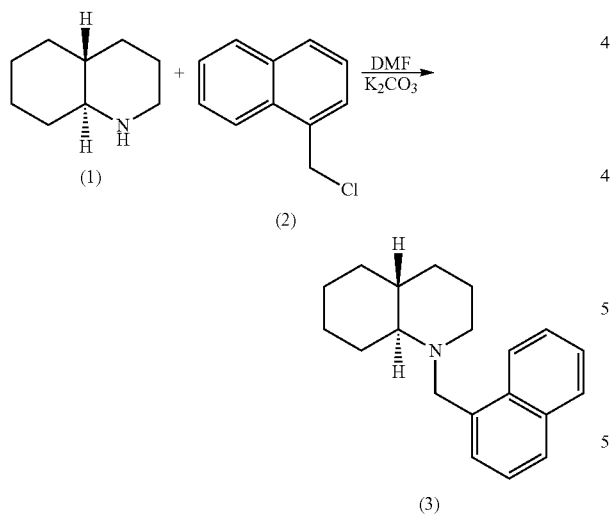

trans-Decahydroquinoline (1) (1.73 g, 12.4 mmol), 1-(chloromethyl)naphthalene (2) (1.98 g, 11.2 mmol) and potassium carbonate (3.72 g, 26.9 mmol) were added to dimethylformamide (16 ml) and heated at 90° C. for 18 hrs. The suspension was cooled, solid filtered and washed with dimethylformamide. Water was added to the filtrate and extracted with diethyl ether. The organic phase was dried over magnesium sulfate and the solvent removed. The residue was purified by column chromatography eluting with 0-5% ethyl acetate in hexane to give (4aR,8aS)-1-naphthalen-1-ylmethyl)decahydroquinoline (3), 2.73 g, (78% yield).

Corrosion Inhibition Efficiency Tests on Metal Surfaces

As shown by the data in the below table, 4aR-8aS-NMDHQ is also an efficient acid corrosion inhibitor.

| | Concentration 4aR-8aS-NMDHQ | | Concn. KI | Weight Loss | | Pitting |
|---|---|---|---|---|---|---|
| Metal type | Wt % | mmol/L | mmol/L | lb/ft² | kg/m² | Index |
| 2205 (b8) | 0.3095 | 11.08 | 0 | 0.0247 | 0.1206 | 1 |
| N80 | 0.3098 | 11.09 | 0 | 0.0190 | 0.0928 | 1 |
| 13Cr | 0.3076 | 11.01 | 0 | 0.0279 | 0.1362 | 2 |
| HS80 | 0.3087 | 11.05 | 0 | 0.0349 | 0.1704 | 2 |

Example 5: NTHQ

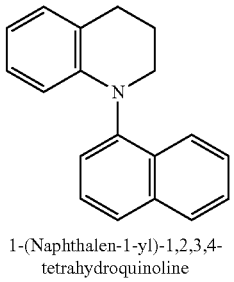 [SMILES: c1ccc2c(c1)CCCN2c1cccc2ccccc12]

1-(Naphthalen-1-yl)-1,2,3,4-tetrahydroquinoline

The structure of NTHQ differs from NMTHQ (Example 1) in that the naphthyl group is directly linked to the nitrogen in the quinoline sub-structure.

NTHQ Synthesis:

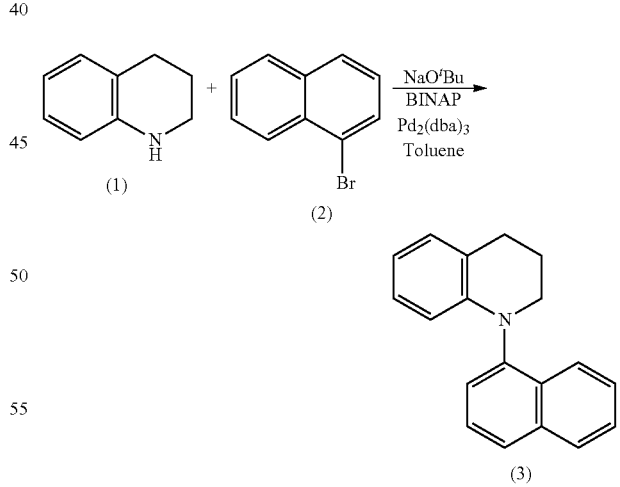

Bis(dibenzylideneacetone)palladium (54 mg) and BINAP (75 mg) were added to toluene and the suspension purged with nitrogen for about 10 mins. Sodium tert-butoxide (262 mg, 2.7 mmol), 1,2,3,4-tetrahydroquinoline (1) (390 mg, 2.9 mmol) and 1-bromonaphthalene (2) (303 mg, 1.46 mmol) were added and the mixture heated at reflux for 4 hr. The catalyst was filtered, washed with ethyl acetate, the filtrate evaporated and the residue purified by column chromatography eluted with 0-3% ethyl acetate in hexane to give 1-(naphthalen-1-yl)-1,2,3,4-tetrahydroquinoline (3), 344 mg (90% yield).

Corrosion Inhibition Efficiency Tests on Metal Surfaces

NTHQ is significantly less soluble than NMTHQ in hydrochloric acid solutions. As a result, a surfactant is required to solubilise NTHQ for corrosion testing purposes. The surfactant used in this example is P2393, a polyoxyethylene tridecyl ether, $C_{13}H_{27}(OCH_2CH_2)_nOH$, where n=10.

As shown by the data in the below table, whilst NTHQ is an example of the generic structures covered by this disclosure, its performance is inferior to that of NMTHQ.

| Metal type | Structure and Concentration of inhibitor | | | Weight Loss | | Pitting Index |
|---|---|---|---|---|---|---|
| | Type | mmol/L | Additive | lb/ft² | kg/m² | |
| 2205 (b5) | NTHQ | 11.00 | P2393, 0.5 wt % | 0.2188 | 1.0683 | 3 |
| HS80 | NTHQ | 11.00 | P2393, 0.5 wt % | 0.0860 | 0.4199 | 1 |
| 2205 (b6) | NMTHQ | 10.97 | — | 0.0091 | 0.0444 | 0 |
| HS80 | NMTHQ | 7.02 | — | 0.0070 | 0.0342 | 0 |

Example 6: NCOTHQ

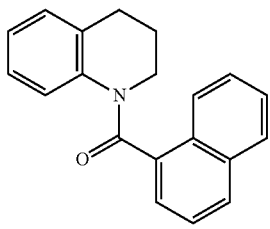

(3,4-Dihydroquinolin-1(2H)-yl)(naphthalene-1-yl)methanone

The structure of NCOTHQ differs from NMTHQ (Example 1) in that the naphthyl group is attached to the nitrogen in the quinoline sub-structure via a methanone group.

NCOTHQ Synthesis:

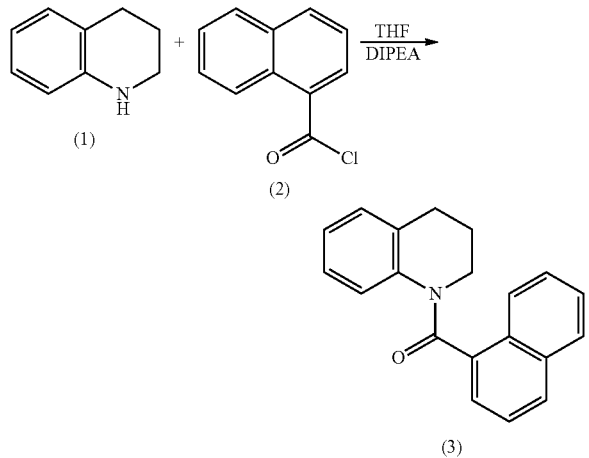

1,2,3,4-Tetrahydroquinoline (1) (2.33 g, 17.5 mmol) and di-isopropylethylamine (3.95 g, 30.6 mmol) were dissolved in THF (30 ml) and 1-naphthoyl chloride (2) (2.78 g, 14.6 mmol) added portion wise over ~2 mins. The mixture was stirred for 3 hr, the precipitated solid filtered and washed with ethyl acetate. The filtrated was extracted with 1M sodium hydroxide, water and brine, dried over sodium sulfate and the solvent removed. The resultant solid was triturated with diethyl ether, solid filtered and washed with diethyl ether and dried to give (3,4-dihydroquinolin-1(2H)-yl)(naphthalene-1-yl)methanone (3), 2.36 g (56% yield).

Corrosion Inhibition Efficiency Tests on Metal Surfaces

NCOTHQ is significantly less soluble than NMTHQ in hydrochloric acid solutions. As a result, a surfactant is required to solubilise NTHQ for corrosion testing purposes. As for example 5 (NTHQ), the surfactant used to solubilise NCOTHQ is P2393, a polyoxyethylene tridecyl ether, $C_{13}H_{27}(OCH_2CH_2)_nOH$, where n=10. Whilst NCOTHQ is an example of the range of structures covered by this disclosure, its acid inhibition performance, in the presence of the solubilising surfactant P2393, is similar to NTHQ (Example 5), i.e. it is an inferior acid corrosion inhibitor as compared to NMTHQ.

Example 7: NMI

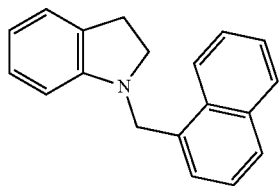

1-(Naphthalen-1-ylmethyl)indoline (3)

Example 7 (NMI) is the naphthyl methyl derivative of indoline as distinct from the equivalent naphthyl methyl derivatives of tetrahydroquinoline (example 1), tetrahydroisoquinoline (example 2) and decahydroquinoline (examples 3 and 4). Similarly, the above structure converts to the protonated form under acid conditions and this reversible process leads to good acid solubility and insolubility (and low toxicity) under neutral pH conditions.

NMI Synthesis:

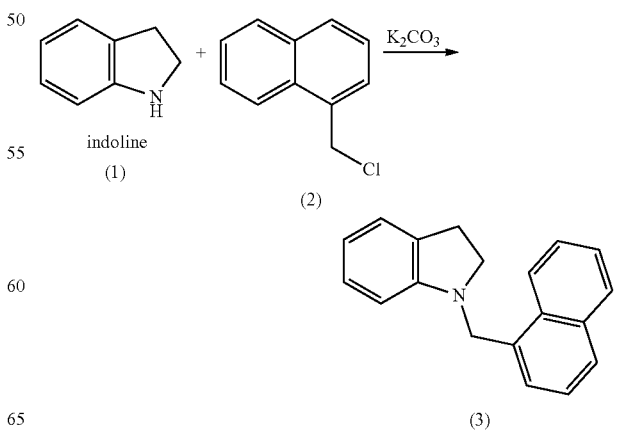

Indoline (1) (1.47 g 12.3 mmol), 1-(chloromethyl)naphthalene (2) (1.98 g, 11.2 mmol) and potassium carbonate (3.72 g, 26.9 mmol) were combined in dimethylformamide (15 ml) and heated at 90° C. for 16 hr. The suspension was cooled, solid filtered, and washed with dimethylformamide. Water was added to the filtrate and extracted with diethyl ether. The organic phase was backwashed with water and brine, dried over sodium sulfate and the solvent removed. The product was purified by column chromatography eluted with 5% ethyl acetate/hexane to give 1-(naphthalen-1-ylmethyl)indoline (3), 2.22 g (76% yield).

Corrosion Inhibition Efficiency Tests on Metal Surfaces

As shown below, NMI is a highly efficient acid corrosion inhibitor on the Duplex stainless steel 2205 and its performance is enhanced by the presence of intensifier potassium iodide.

| Metal type | Concentration of NMI inhibitor | | Concn KI | Weight Loss | | Pitting Index |
|---|---|---|---|---|---|---|
| | Wt % | mmol/L | mmol/L | lb/ft² | kg/m² | |
| 2205 (b9) | 0.1304 | 5.03 | 0 | 0.0477 | 0.2329 | 3 |
| 2205 (b9) | 0.1308 | 5.04 | 20 | 0.0026 | 0.0127 | 0 |

Example 8: HINNME

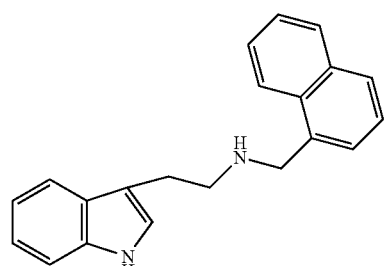

2-(1H-Indol-3-yl)-N-(naphthalene-1-ylmethyl)ethan-1-amine (3)

Example 8 (HINNME) is a naphthyl methyl derivative of the monoamine alkaloid tryptamine. In this case, the primary amine group within the tryptamine sub-structure is reacted with 1-naphthaldehyde. The product incorporates two nitrogen atoms each of which can be protonated in acid to enhance solubility and corrosion inhibition efficiency.

HINNME Synthesis:

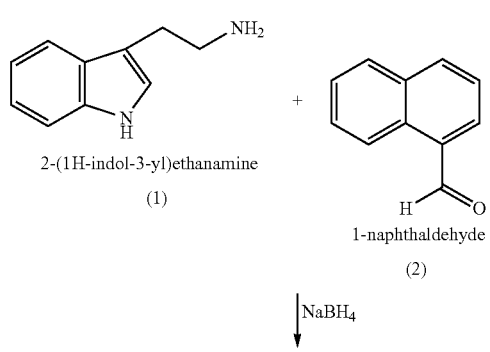

2-(1H-indol-3-yl)ethanamine (1) + 1-naphthaldehyde (2)

↓ NaBH₄

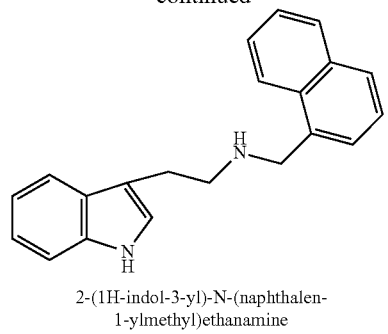

2-(1H-indol-3-yl)-N-(naphthalen-1-ylmethyl)ethanamine (3)

Tryptamine (1) (2.3 g, 14.3 mmol) was added portion wise to a solution of naphthaldehyde (2) (2.94 g, 18.8 mmol) in methanol (25 ml) at 5° C. The solution was stirred at ambient temperature for 4 hr, solid filtered and washed with methanol. The solution was suspended in methanol and sodium borohydride (0.5 g, 13.2 mmol) added portionwise over 20 mins with cooling. The mixture was stirred overnight and solvent removed. The residue was partitioned between ethyl acetate and saturated sodium bicarbonate solution, the organic phase was removed washed sequentially with and saturated sodium bicarbonate solution, water and brine, dried over sodium sulfate and the solvent removed. The material was applied to a silica gel column and eluted with 5-10% (2M ammonia in methanol/dichloromethane)/dichloromethane to give 2-(1H-indol-3-yl)-N-(naphthalene-1-ylmethyl)ethan-1-amine (3), 3.65 g (84%).

Corrosion Inhibition Efficiency Tests on Metal Surfaces

| Metal type | Concentration of HINNME inhibitor* | | Concn KI | Weight Loss | | Pitting Index |
|---|---|---|---|---|---|---|
| | Wt % | mmol/L | mmol/L | lb/ft² | kg/m² | |
| 2205 (b9) | 0.1542 | 5.13 | 0 | 0.0299 | 0.1460 | 2 |
| 2205 (b9) | 0.1500 | 4.99 | 20 | 0.0034 | 0.0166 | 0 |

It is noted that in both tests, 5 mL of the mutual solvent ethylene glycol butyl ether (2-butoxyethanol) was also added to the 200 mL 4 mol/L HCl solution in order to enhance the solubility of the inhibitor HINNME.

Example 9: NMHIE

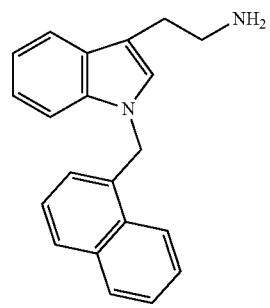

2-(1-(Naphthalene-1ylmethyl)-1H-indol-3-yl)ethan-1-amine (3)

Example 9 (NMHIE) is a naphthyl methyl derivative of the monoamine alkaloid tryptamine but in this case, the nitrogen within indolyl sub-structure is reacted with 1-(chloromethyl)naphthalene. As for HINNME (Example 9), the product incorporates two nitrogen atoms each of which can be protonated in acid to enhance solubility and corrosion inhibition efficiency.

NMHIE Synthesis:

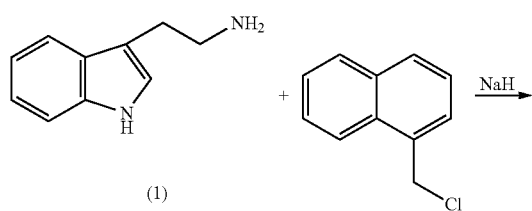

(1)

(2)

(3)

Tryptamine (1) (0.7 g, 4.36 mmol) was dissolved in dimethylformamide (3.5 ml) and cooled to 10° C. Sodium hydride (60% in oil, 200 mg, 5 mmol) was added portionwise and stirred at 10° C. for 45 mins. A solution of 1-(chloromethyl)naphthalene (2) (842 mg, 4.76 mmol) in dimethylformamide (3.5 ml) was added dropwise then the mixture was stirred at ambient temperature overnight. The mixture was poured in water (20 ml), liquor decanted from precipitate which was dissolved in ethyl acetate and extracted with water. The organic phase was dried over sodium sulfate, the solvent removed and material applied to a silica column eluted with 2.5-5% (2M ammonia in methanol: dichloromethane)/dichloromethane to give 2-(1-(Naphthalene-1ylmethyl)-1H-indol-3-yl)ethan-1-amine (3), 819 mg (62% yield).

Corrosion Inhibition Efficiency Tests on Metal Surfaces

| Metal type | Concentration of NMHIE inhibitor | | Concn KI | Weight Loss | | Pitting Index |
|---|---|---|---|---|---|---|
| | Wt % | mmol/L | mmol/L | lb/ft² | kg/m² | |
| 2205 (b9) | 0.1542 | 5.13* | 0 | 0.0927 | 0.4526 | 5 |
| 2205 (b9) | 0.1542 | 5.13** | 0 | 0.1084 | 0.5293 | 3 |
| 2205 (b9) | 0.1500 | 4.99* | 20 | 0.0090 | 0.0439 | 0 |

*It is noted that 0.5 wt % P2393, a polyoxyethylene tridecyl ether, $C_{13}H_{27}(OCH_2CH_2)_nOH$, where n = 10, was added to the 200 mL 4 mol/L HCl solution in order to enhance the solubility of the inhibitor NMHIE.
**It is further noted that 5 mL of the mutual solvent ethylene glycol butyl ether (2-butoxyethanol) was added to the 200 mL 4 mol/L HCl solution in order to enhance the solubility of the inhibitor NMHIE.

Example 10: NMM

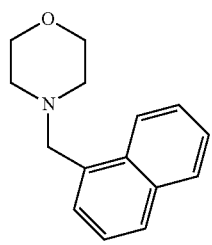

4-(Naphthalene-1-ylmethyl)morpholine

NMM Synthesis

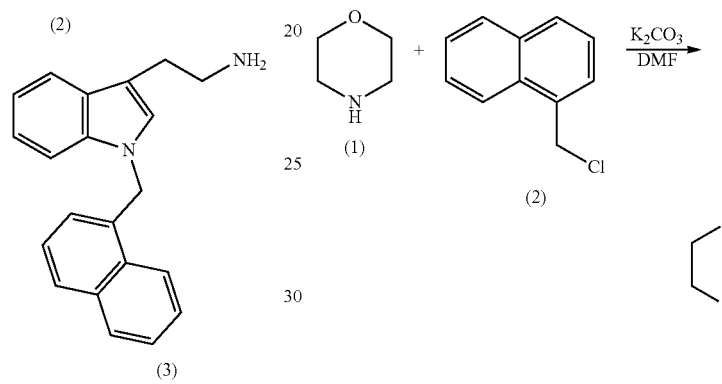

(1)

(2)

(3)

Morpholine (1) (1.3 g, 14.9 mmol), 1-(chloromethyl) naphthalene (2), (2.37 g, 13.4 mmol), potassium iodide (20 mg) and potassium carbonate (4.2 g, 30 mmol) were added to dimethylformamide (30 ml) and the suspension heated at 85° C. overnight. The solid was filtered and washed with dimethylformamide. Water and diethyl ether were added to the filtrate, the organic phase removed, extracted with water and brine, dried over sodium sulfate and the solvent removed. The crude product was purified using column chromatography eluting with 20-30% diethyl ether in hexane to give 4-(naphthalene-1-ylmethyl)morpholine (3), 2.3 g (75% yield).

Corrosion Inhibition Efficiency Tests on Metal Surfaces

| Metal type | Concentration of NMM inhibitor | | Concn KI | Weight Loss | | Pitting Index |
|---|---|---|---|---|---|---|
| | Wt % | mmol/L | mmol/L | lb/ft² | kg/m² | |
| 2205 (b9) | 0.1402 | 5.05 | 0 | 0.1160 | 0.5664 | 5 |
| 2205 (b9) | 0.1397 | 5.04 | 20.12 | 0.0114 | 0.0557 | 2 |

Example 11—Comparison Tests

Figure 4:
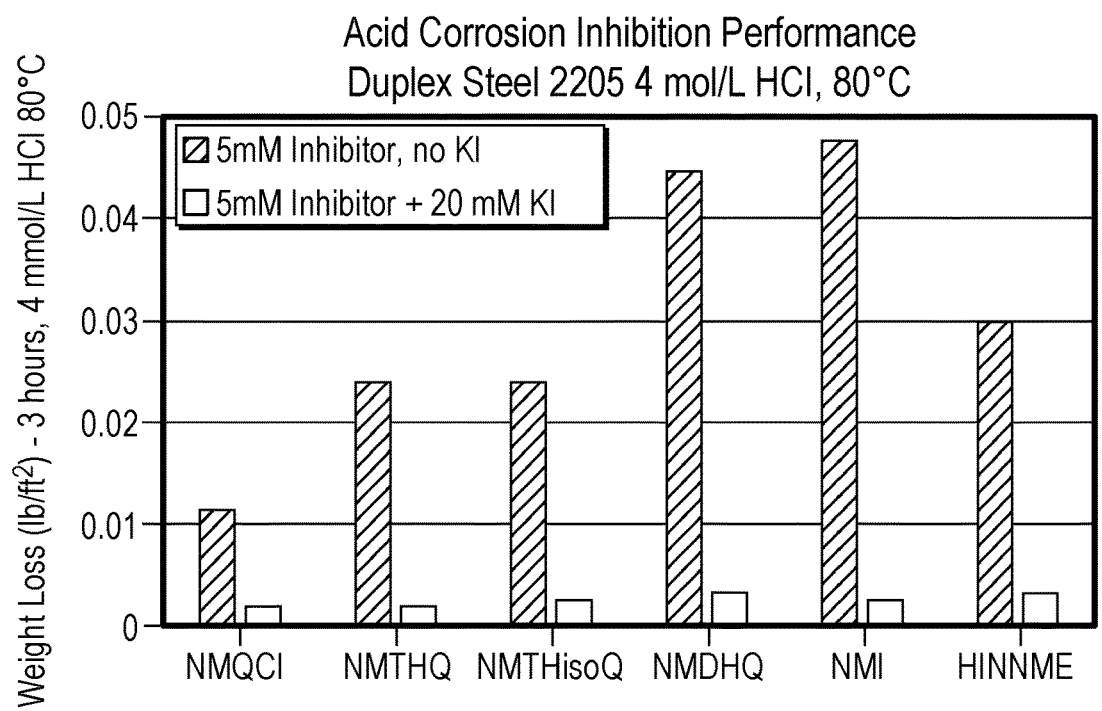
FIG. 4 is a bar chart showing comparison weight loss results in example 11 below.

The acid corrosion inhibition performance of the known acid corrosion inhibitor NMQCl and examples of the present disclosure have been tested on the Duplex stainless steel 2205, with and without potassium iodide addition. The results are shown in FIG. 4.

Example 12—Molecular Modelling

Molecular modelling is used to calculate a few different parameters in order to better understand and compare protonated NMHQ and NMQCl as acid corrosion inhibitors.

Energies of the highest occupied molecular orbital (HOMO) and the lowest unoccupied molecular orbital (LUMO) were calculated using local density approximation exchange correlation functional implemented in the Amsterdam Density Functional (ADF2013.01) program. The Slater basis sets with Double-Zeta plus one polarization functions were used. The frozen core approximation applied was large. During the calculation process, the geometry of the molecule was also optimized.

Log P is calculated with Marvin Sketch using a weighted method from three database, Viswanadhan and Ghose1, Klopman's paper2, and PHYSPROP©. The electrolyte concentration is set to 0.1 M of Chloride anion and 0.1 M of Sodium or Potassium cation.

Key factors influencing inhibition efficiency include conformation of molecule, energy levels such as HOMO, LUMO, fermi energy level $E_{(fermi)}$, and band gap, and solubility.

Figure 5:
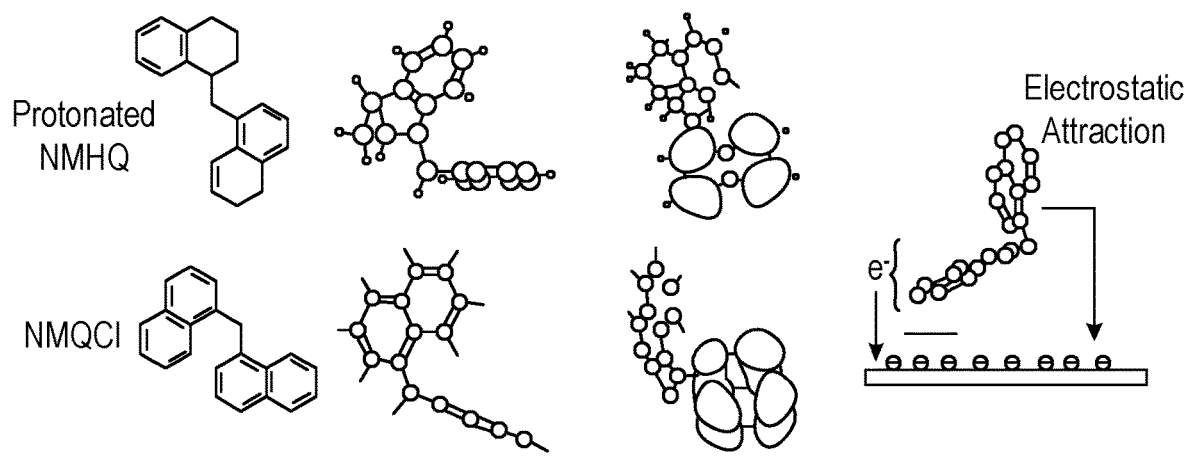
FIG. 5 is molecular modelling results in example 12 below.

As shown in FIG. 5, molecular modelling illustrates that NMHQ and NMQCl have similar conformation. In both inhibitor compounds, substructure B, the naphthyl group, is the electron donating HOMO. As shown in FIG. 5, the conformation of both compounds would allow their HOMO to lie flat on the metal substrate for electron sharing.

Log P is a measure of hydrophobicity as defined by:

$$\text{Log } P_{octanol/water}=\log([\text{solute}]_{octanol}/[\text{solute}]_{water})$$

The protonated form of NMHQ has a log P value of 2.21 whereas NMHQ is significantly more hydrophobic (log P=5.28). Thus, the non-protonated form NMHQ is insoluble under neutral pH conditions.

Molecular modelling gives the following results for NMHQ, protonated NMHQ and NMQCl:

| Inhibitors | pKa | LogP | Ef/H | Eg/H |
|---|---|---|---|---|
| NMHQ | 4.38 | 5.28 | −0.145 | 0.084 |
| Protonated NMHQ | N/A | 2.21 | −0.286 | 0.119 |
| NMQCl | N/A | 0.55 | −0.315 | 0.043 |

N/A—not applicable

As we can see from the above table, protonated NMHQ has a higher log P and Fermi level than NMQCl, both of which would lead to superior acid inhibition ability. However, NMQCl has a smaller band gap than protonated NMHQ, which would lead to superior acid inhibition ability. In view of the latter statements, overall molecular modelling suggests protonated NMHQ should show equal or better inhibition performance than NMQCl.

In addition, NMHQ is protonated and thus soluble in acid which allows it to act as an acid corrosion inhibitor. Meanwhile, NMHQ is insoluble at neutral or alkaline pH due to de-protonation. This means NMHQ is insoluble in spent acid and formation brine when fluids flow back to the surface resulting in zero aquatic toxicity.

Example 13—Electrochemistry Experiments

Dynamic flow conditions downhole have been recreated in the laboratory using Rotating Cylinder Electrodes (RCE). 5 mM of NMQCl and NMHQ have been tested at 2000 rpm and 80° C. in the presence of 10 mM KI and 4 mol/L HCl. Charge transfer resistance, $R_{ct}$, is measured. Charge transfer resistance, $R_{ct}$, is a measure for corrosion resistance, and is inversely proportional to corrosion rate (CR). Therefore $1/R_{ct}$ is proportional to CR. A higher $1/R_{ct}$ means a faster corrosion rate, so indicating the corrosion inhibitor is less effective.

Figure 6:
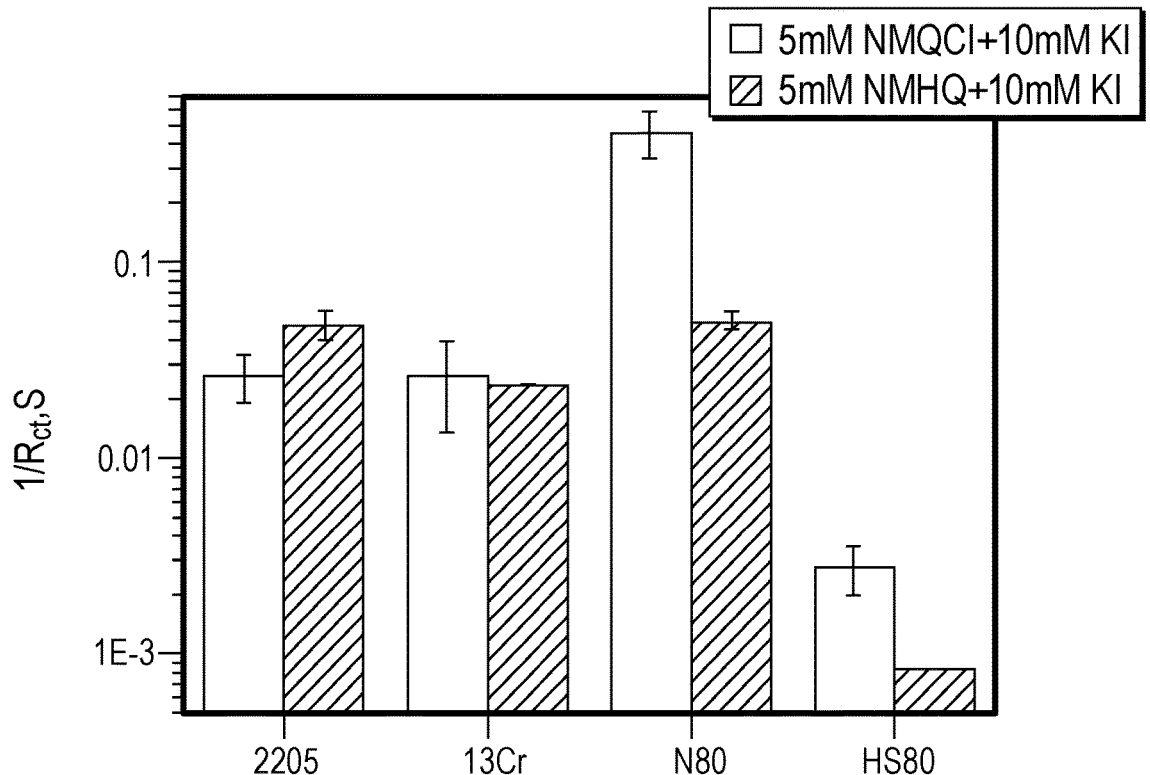
FIG. 6 is electrochemistry experiment results in example 13 below.

The results $1/R_{ct}$ are plotted in FIG. 6. It shows very similar results for NMQCl and NMHQ on 2205 and 13Cr. It also shows that NMHQ is a more effective inhibitor on both C-steels, N80 and HS80. In particular, corrosion rate in the presence of NMHQ is significant lower on HS80.

Example 14—Toxicity Tests

The acute toxicity of NMHQ to the marine algae *Skeletonema costatum* was tested. Cultures of the algae *Skeletonema costatum* were exposed to a series of concentrations of NMHQ. The test was carried out according to ISO protocol 'ISO 10253 Water quality—Marine algal growth inhibition test with *Skeletonema costatum* and *Phaeodactylum tricornutum*'.

In addition to blank, concentrations of 10, 100, 1000 mg/L (WAF) in sea water were tested. The results were: EC50(72 h)>1000 mg/L; EC90(72 h)>1000 mg/L; NOEC(72 h)=1000 mg/L.

This test confirms that NMHQ in seawater under neutral conditions (pH 7.7-8.3) results in zero aquatic toxicity, as expected due to its insolubility.

The invention claimed is:

1. A corrosion inhibiting compound with a general structure A-B,
    wherein A comprises a heterocyclic ring system comprising a plurality of cyclic Carbon atoms and at least one cyclic Nitrogen atom, wherein the at least one cyclic Nitrogen atom is neutral under neutral conditions and protonatable under acidic conditions;
    wherein B comprises at least two unsaturated Carbon atoms; and
    wherein at least one of:
        A is tetrahydroquinoline;
        B comprises a homocyclic ring system;
        B comprises two or three fused rings; or
        B comprises a plurality of aromatic rings; or
        B is naphthyl.

2. The corrosion inhibiting compound according to claim 1, wherein A and B are connected via a linking Nitrogen atom, the linking Nitrogen atom being one of the at least one cyclic Nitrogen atom in A.

3. The corrosion inhibiting compound according to claim 1, wherein A and B are connected directly or via X, and wherein X comprises one or more Carbon atoms.

4. The corrosion inhibiting compound according to claim 3, wherein X is methylene.

5. The corrosion inhibiting compound according to claim 1, wherein A comprises one or two or three rings.

6. The corrosion inhibiting compound according to claim 1, wherein A comprises two or three fused rings.

7. The corrosion inhibiting compound according to claim 6, wherein at least one of the fused rings is aromatic.

8. The corrosion inhibiting compound according to claim 1, wherein B comprises a polymerisable group.

9. The corrosion inhibiting compound according to claim 1, further comprising a polymerisable group attached to A and/or B.

10. A method of inhibiting corrosion of a metal surface exposed to an acidic solution comprising including in the solution a corrosion inhibiting compound according to claim 1.

11. A method of using a corrosion inhibiting compound according to claim 1 comprising adding the corrosion inhibiting compound to minimize corrosion of metal surfaces in acidic solutions.

12. A method of using a corrosion inhibiting compound according to claim 1 comprising including the corrosion inhibitor compound in an oil and gas industry application.

13. A method of using a corrosion inhibiting compound according to claim 1 comprising adding the corrosion inhibiting compound to water.

14. A corrosion inhibiting compound with a general structure A-B,
   wherein A comprises a heterocyclic ring system comprising a plurality of cyclic Carbon atoms and at least one cyclic Nitrogen atom, wherein the at least one cyclic Nitrogen atom is neutral under neutral conditions and protonatable under acidic conditions;
   wherein A comprises two or three fused rings;
   wherein at least one of the fused rings is fully saturated; and
   wherein B comprises at least two unsaturated Carbon atoms.

15. A corrosion inhibiting compound with a general structure A-B,
   wherein A comprises a heterocyclic ring system comprising a plurality of cyclic Carbon atoms and at least one cyclic Nitrogen atom, wherein the at least one cyclic Nitrogen atom is neutral under neutral conditions and protonatable under acidic conditions;
   wherein B comprises at least two unsaturated Carbon atoms;
   wherein A and B are connected via a linking Nitrogen atom, the linking Nitrogen atom being one of the at least one cyclic Nitrogen atom in A; and
   wherein one or more of the plurality of cyclic Carbon atoms in A is directly connected to the linking Nitrogen atom and the one or more of the plurality of cyclic Carbon atoms is saturated.

* * * * *